United States Patent
Spanier et al.

(10) Patent No.: US 9,669,144 B2
(45) Date of Patent: Jun. 6, 2017

(54) CATHETER SYSTEM AND INTRAVASCULAR BLOOD PUMP COMPRISING SAID CATHETER SYSTEM

(71) Applicant: ABIOMED EUROPE GmbH, Aachen (DE)

(72) Inventors: Gerd Spanier, Aachen (DE); Thorsten Siess, Aachen (DE)

(73) Assignee: ABIOMED EUROPE GMBH, Aachen (DE)

( * ) Notice: Subject to any disclaimer, the term of this patent is extended or adjusted under 35 U.S.C. 154(b) by 0 days.

(21) Appl. No.: 14/396,719

(22) PCT Filed: Apr. 25, 2013

(86) PCT No.: PCT/EP2013/058636
§ 371 (c)(1),
(2) Date: Oct. 23, 2014

(87) PCT Pub. No.: WO2013/160405
PCT Pub. Date: Oct. 31, 2013

(65) Prior Publication Data
US 2015/0087890 A1 Mar. 26, 2015

(30) Foreign Application Priority Data

Apr. 27, 2012 (DE) .................. 10 2012 207 056

(51) Int. Cl.
| *A61M 1/10* | (2006.01) |
| --- | --- |
| *A61B 5/00* | (2006.01) |
| *A61B 5/0215* | (2006.01) |
| *A61M 25/01* | (2006.01) |
| *A61M 1/12* | (2006.01) |

(52) U.S. Cl.
CPC .......... *A61M 1/1086* (2013.01); *A61B 5/0215* (2013.01); *A61B 5/02154* (2013.01); *A61B 5/6852* (2013.01); *A61M 1/125* (2014.02); *A61M 25/01* (2013.01);
(Continued)

(58) Field of Classification Search
CPC ........................... A61M 1/1086; A61M 1/125
See application file for complete search history.

(56) References Cited

U.S. PATENT DOCUMENTS

| 5,565,976 A | 10/1996 | Fieggen et al. |
| --- | --- | --- |
| 2009/0149810 A1 | 6/2009 | Ring et al. |
| 2011/0040231 A1 | 2/2011 | Gregory |

FOREIGN PATENT DOCUMENTS

WO    WO-2011/039091    4/2011

OTHER PUBLICATIONS

International Preliminary Report on Patentability for PCT/EP2013/058636 mailed Apr. 10, 2014.
(Continued)

*Primary Examiner* — Joseph Dietrich
(74) *Attorney, Agent, or Firm* — White & Case LLP

(57) ABSTRACT

A catheter (20), which can be part of an intravascular blood pump, possesses a kink sensor which extends over the total length of the catheter and comprises an optical fiber (28A). The optical fiber is attached to an evaluation device (100) which evaluates a preset light quantity transmitted through the optical fiber as to whether a part of the light quantity is coupled out of the optical fiber along the length of the optical fiber. This is interpreted as a kink event and displayed. The optical fiber preferably utilized for the kink sensor is the optical fiber of an optical pressure sensor.

13 Claims, 2 Drawing Sheets

(52) U.S. Cl.
    CPC .......... *A61B 2562/0233* (2013.01); *A61B 2562/0247* (2013.01); *A61M 2025/0166* (2013.01); *A61M 2209/02* (2013.01)

(56) References Cited

OTHER PUBLICATIONS

International Search Report for PCT/EP2013/058636 mailed Jul. 10, 2014.

CATHETER SYSTEM AND INTRAVASCULAR BLOOD PUMP COMPRISING SAID CATHETER SYSTEM

CROSS-REFERENCE TO RELATED APPLICATIONS

This application is the U.S. National Stage of International Patent Application Number PCT/EP2013/058636, filed on Apr. 25, 2013, which claims priority to German Patent Application No. 10 2012 207 056.7, filed on Apr. 27, 2012. The entire contents of the foregoing applications are hereby incorporated herein by reference.

TECHNICAL FIELD

This invention relates in general to a system comprising a catheter, in particular a pressure-measuring catheter, and in particular to an intravascular blood pump having such a catheter system.

BACKGROUND ART

WO 2011/039091 A1 describes in connection with a heart support system a pressure-measuring catheter which has a catheter hose and a pressure sensor for measuring the pressure distally of the catheter hose. Concretely, the pressure-measuring catheter has an optical pressure sensor and an elongate tube made of metal or a high-strength plastic, for example PEEK, through which a loosely laid optical fiber of the optical pressure sensor extends. At the anterior (distal) end of the pressure-measuring catheter there is located a sensor head which works on the Fabry-Perot principle. The sensor head possesses a cavity which is terminated by a thin, pressure-sensitive glass membrane, on the one hand, and into which the end of the optical fiber protrudes, on the other hand. The pressure-sensitive glass membrane is deformed in dependence on the size of the pressure acting on the sensor head. Through the reflection on the glass membrane, the light exiting from the optical fiber is modulatingly reflected and fed into the optical fiber again. At the proximal end of the optical fiber there is located an evaluation unit having an integrated CCD camera, which evaluates the obtained light in the form of an interference pattern. In dependence thereon, a pressure-dependent electrical signal is generated. Altogether this is thus an optoelectronic pressure sensor.

The pressure-measuring catheter is employed in connection with intravascular heart support systems, such as for example an intra-arterial balloon pump (IABP) or an intravascular rotary blood pump, by first advancing the relevant heart support system to the desired place in the patient's vascular system, i.e. for example into the aorta or into a heart chamber, by means of a catheter hose. The pressure-measuring catheter including the tube surrounding the optical fiber is displaceable relative to this catheter hose in its longitudinal direction and is subsequently introduced into the lumen of the catheter hose, advanced through the catheter hose and exits from its end. When the sensor head has reached the intended measurement location, the tube of the pressure-measuring catheter is withdrawn, but can also remain in situ as a permanent part of the pressure-measuring catheter. In connection with a rotary blood pump, it is proposed to push the pressure-measuring catheter far beyond the distal end of the catheter hose past the pump device of the rotary blood pump, so that it crosses the aortic valve and protrudes with its sensor head into the left ventricle to thereby measure the ventricular pressure.

A problem when navigating within the vascular system by means of catheters is curvatures, vessel branchings or obstacles to be crossed, such as for example cardiac valves. At such places the catheter can jam and bend back on itself due to its flexibility instead of pushing forward further. This is known as "kinking". Such kinking is not always perceptible to the treating physician. Since the physiological pressure signals delivered by the pressure sensor are frequently ambiguous, it can hence happen that the physician fails to recognize the misplacement of the catheter, but mistakenly assumes that the catheter has reached the desired placement.

The object of the invention is hence to avoid mistakenly laying a catheter in a vessel of the patient, be it a blood vessel or another vessel, in the kinked state.

This object is achieved by the features of the independent claim. Claims dependent thereon state advantageous developments and embodiments of the invention.

SUMMARY

According to a preferred embodiment of the invention, the catheter is equipped with a kink sensor. As soon as the catheter kinks, this is detected and evaluated in an evaluation device, which can for example generate a corresponding signal for the treating physician. The kink sensor can work absolutely, i.e. when a preset kink event occurring for example as of a defined bend radius of the catheter is detected, an alarm is triggered. However, it can also work relatively and display the degree of kinking, with an alarm being triggered upon reaching of a limiting value, where applicable.

The kink sensor preferably extends over the total length of the catheter and can detect a kinking of the catheter over its total length. In this manner, those kink events are also detected that occur for example when the distal end of the catheter jams but the catheter kinks far away from the catheter tip at a place in the vascular system where there is enough room therefor, for example at a relatively large vessel branching.

According to a particularly preferred exemplary embodiment, the kink sensor comprises at least one optical fiber. Optical fibers transmit light virtually losslessly even in the bent state. As of a predetermined bend radius, however, a part of the light couples out of the optical fiber laterally. What the critical bend radius is depends on the material of the optical fiber, here specifically on the refractive indices of the glass layers, and the material bordering on the surface of the optical fiber. This depends in particular on the structure of the glass fiber, specifically the configuration of the radially symmetric reflective layer in the glass fiber, which is formed by the boundary surface between the optical-fiber core and the optical-fiber cladding. The configuration of the glass fiber may be either gradual (graded-index fiber) or involve a direct transition (step-index fiber). Glass fibers are furthermore normally plastic-coated, e.g. with polyimide, on the outside for their mechanical protection.

The special advantage of employing an optical fiber as a kink sensor is that an optical fiber is of simple structure and accordingly cheap to manufacture, and that it in particular enables a kinking over the total length range of the catheter in which the optical fiber is laid. Conversely, a specific part of the catheter, such as the catheter tip, can also be designed to be especially kink-sensitive, so that kinking is detected preferably there.

Through a suitable choice of the material pairing between the light-transmitting optical-fiber core and the material surrounding the optical-fiber core, it is possible to preadjust the sensitivity of the kink sensor within certain limits, so that light actually couples out of the optical fiber as of a preset bend radius. In this manner, or by using a plurality of fibers of different length or with segments transmitting light differently, it is even possible to obtain a location-dependent detection of bend.

The optical fiber is accordingly attached to an evaluation device which is arranged for evaluating a preset light quantity transmitted through the optical fiber as to whether a part of the light quantity is coupled out of the optical fiber along the length of the optical fiber. For this purpose, light is preferably coupled into the proximal end of the optical fiber, reflected at the distal end of the optical fiber, and the quantity of reflected light incoming at the proximal end measured. If this light quantity and consequently the signal-to-noise ratio changes, it is to be concluded that a part of the light quantity has been coupled out over the length of the optical fiber. As soon as this coupled-out part of the light quantity reaches or exceeds a preset limiting value, which can also be set very low, a kinking of the catheter can be inferred. The evaluation device then preferably generates an alarm in an optical, acoustic or other manner. If the catheter is accordingly designed, the light guide can be kinked such that this is done reversibly without breakage, so that the user is put in a position to revise strong bends or kinks by suitable manipulation.

The employment of an optical fiber as a kink sensor is accordingly very reliable. It is important, however, that the optical fiber itself does not break when a kink event occurs. In the case of plastic fibers, stress whitenings can occur, and in the case of glass fibers, the fibers as a whole can break. This, too, would in effect be correctly identified as a kink event by the evaluation device. However, the kink sensor would then be destroyed and no longer usable. To ensure continuing operability after extreme kink events, it is hence advantageous to configure optical fibers made of plastic with a diameter of 250 .mu.m or less. If the optical fiber comprises a glass fiber, the diameter of the optical fiber should amount to no more than 150 .mu.m. The stated diameter values respectively relate to the total diameter of the optical fiber including any coatings of the light-transmitting optical-fiber core. Breaks and also stress whitenings of the fibers can likewise be detected. This makes it possible to notify the user of the failure of the measurement device and thus avoid further placement attempts being made with a defective system. This is important for use as a medical sensor.

The optical fiber is preferably laid freely movably in the catheter. However, it can be laid freely movably in a separate lumen for protection against other devices laid in the catheter. The lumen in which the optical fiber extends preferably consists of a material comprising a shape-memory alloy, in particular of so-called "nitinol". Shape-memory alloys (SMAs) are often also referred to as memory metals because they seem to "remember" an earlier shape in spite of being strongly deformed subsequently. This remembering process is temperature-dependent. The special benefit of a shape-memory alloy as the material for the lumen of the optical fiber does not lie in the material's temperature-dependent ability to remember, however, but in the fact that shape-memory alloys show superelastic behavior. Thus, the lumen itself in which the optical fiber is received also moves back to its initial shape elastically again after a kink event.

The outer diameter of such a lumen made of a shape-memory alloy preferably amounts to 330 μm or less, particularly preferably 220 μm or less, and the inner diameter preferably amounts to 230 μm or less, or particularly preferably 150 μm or less. Nitinol tubelets, i.e. tubelets made of a corresponding nickel-titanium alloy with shape-memory properties, are commercially available with the above-mentioned diameter dimensions.

The catheter can alternatively also be made of a polymer, and here preferably polyurethane, since this material also briefly has a shape memory and can largely reversibly "unkink" itself. The polymer material is preferably anti-friction-coated on the inside, and the optical fiber laid freely therein.

The invention is especially advantageously integratable into an optical pressure sensor which already itself comprises an optical fiber, such as for example the above-described optical pressure sensor working on the Fabry-Perot principle. Since the optical fiber is already present in the optical pressure sensor and the light transmitted through the optical fiber is evaluated by an evaluation device anyway, the evaluation device only needs to be adapted such that it is checked whether a part of the light quantity transmitted through the optical fiber is coupled out of the optical fiber.

A corresponding optical pressure sensor can be configured as an independent catheter which is either introduced into the patient's vascular system in isolation or is part of a larger catheter. It is especially advantageous when the kink sensor or the optical pressure sensor acting as a kink sensor is part of a catheter of an intravascular blood pump with which the blood pump is navigated within the patient's vascular system. In this case, the kink sensor, i.e. the optical fiber or the lumen in which the optical fiber is laid, is firmly connected to the blood pump. For this purpose, the kink sensor is laid along the catheter, either on the inside and/or on the outside, and at least the sensor head, i.e. the distal end of the kink sensor, is firmly connected to the blood pump in order that its kink-sensor function can be reliably performed.

At the same time, the kink sensor can also extend beyond the catheter along the blood pump, for example to the distal end of the blood pump. This is expedient for example in cases where the blood pump possesses at its distal end a flexible flow cannula which is itself in danger of kinking. This embodiment is especially advantageous, since for example the immediate valvular situation can be detected by bending the cannula or the distal end of the cannula so that the cardiac valve can be crossed retrograde without any additional imaging methods. In detail, this means that the sensor not only documents the transition from the pressure before the valve to the pressure behind the valve, but additionally supports the valve crossing in an exactly location-dependent manner through deformation. Monitoring the bend radius of the cannula makes it possible to indirectly measure the force of the pressure against the valve and thus enable an atraumatic crossing.

BRIEF DESCRIPTION OF THE DRAWINGS

Hereinafter the invention will be described by way of example with reference to the accompanying drawings. Therein are shown.

DETAILED DESCRIPTION

Figure 1:
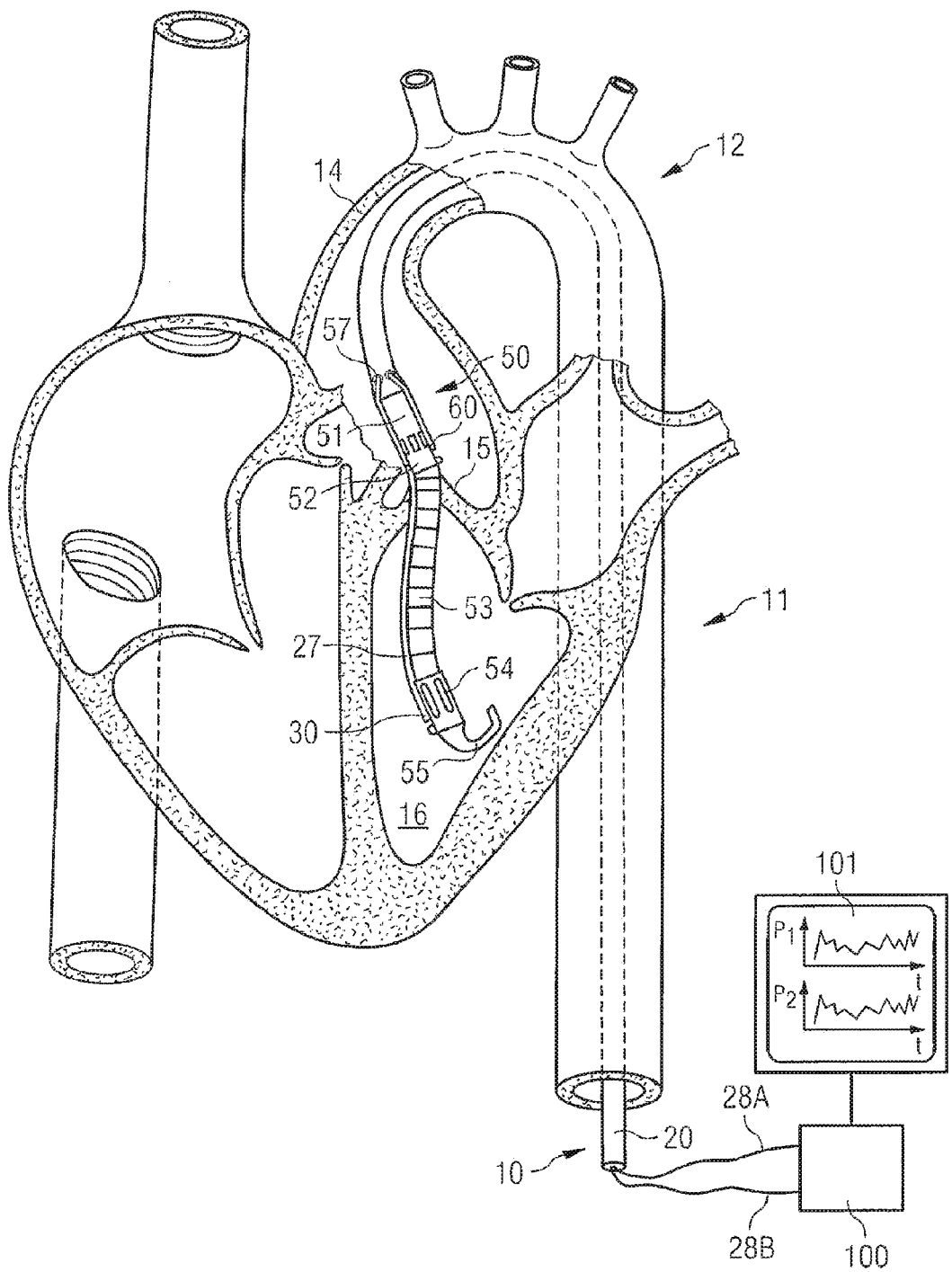
FIG. 1 a blood pump laid through the aorta, which extends through the aortic valve into the left ventricle and has an integrated pressure and kink sensor, and FIG. 2 an optical pressure sensor having an optical fiber.

FIG. 1 shows an intravascular blood pump having a catheter 10 which is introduced into the descending aorta 11 retrograde. The descending aorta is part of the aorta 12 which first ascends from the heart and then descends and has the aortic arch 14. At the beginning of the aorta 12 there is located the aortic valve 15 which connects the left ventricle 16 to the aorta 12 and through which the intravascular blood pump extends. The intravascular blood pump comprises in addition to the catheter 10 a rotary pumping device 50 fastened at the distal end of the catheter hose 20 and having a motor section 51 and a pump section 52 disposed at an axial distance therefrom, as well as a flow cannula 53 protruding in the distal direction from the inflow end of the pump section 52 and having a suction inlet 54 located at its end. Distally of the suction inlet 54 there is provided a soft-flexible tip 55, which can be configured for example as a "pigtail" or in a J shape. Through the catheter hose 20 there extend different lines and devices which are important for operating the pumping device 50. Of these, FIG. 1 only shows two optical fibers 28A, 28B which are attached at their proximal end to an evaluation device 100. These optical fibers 28A, 28B are respectively part of an optical pressure sensor whose sensor heads 30 and 60 are located on the outside on the housing of the pump section 52, on the one hand, and on the outside on the suction inlet 54, on the other hand. The pressure transmitted by the sensor heads 30 and 60 is converted into electrical signals in the evaluation device 100 and displayed e.g. on a display screen 101.

The measurement of both the aortic pressure by means of the sensor head 60 and the ventricular pressure by means of the sensor head 30 makes possible, in addition to the actual pressure signal, e.g. a contractility measurement by which the recovery of the heart is measured, as well as the establishment of the pressure difference which is used for computing the flow of the pumping device 50.

The distal sensor head 30 can moreover extend into the soft-flexible tip 55, thereby detecting the pressure transition from the aortic pressure to the ventricular pressure at the tip 55 of the pump specifically upon retrograde valve crossing. Moreover, this enables the bending of the tip 55 to be detected very sensitively, which makes a simpler valve crossing possible. When the pump is located near the wall, as in FIG. 1, an excessive pressure on the cardiac wall as a result of the bending or kinking can moreover be detected. The latter can also lead to the inlet sucking on cardiac structures. Detection of this state can be revised by the user by rotating or withdrawing the pump.

Figure 2:
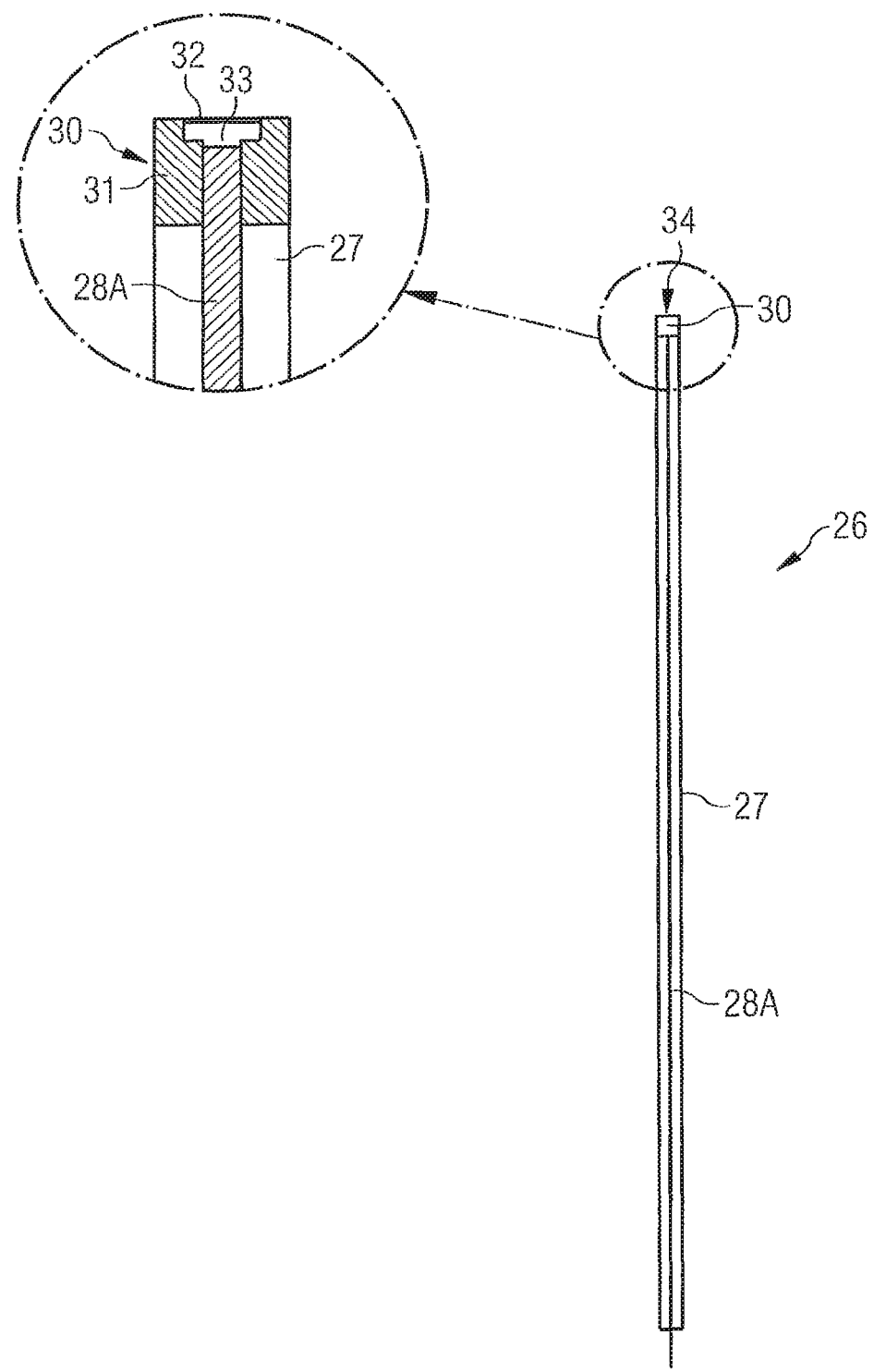

The principle of electro-optical pressure measurement will be explained more closely hereinafter with reference to FIG. 2. FIG. 2 shows a pressure-measuring catheter 26 having a lumen 27 in which an optical fiber 28A (which might also be a plurality of optical fibers) is freely movable. The lumen 27 can preferably consist of nitinol or another shape-memory alloy or a polymer hose, exit from the catheter hose 20 at an exit point 57, and be guided along the flexible flow cannula 53 on the outside. Within the catheter hose 20 the separate sliding tube 27 can be omitted. At the distal end 34 of the optical fiber 28A the pressure-measuring catheter has a sensor head 30 having a head housing 31 which contains a thin glass membrane 32 which terminates a cavity 33. The optical fiber 28A does not necessarily have to terminate the cavity here. It must only be ensured that the light is coupled into and out of the fiber 28A in a low-loss manner. The glass membrane 32 is pressure-sensitive and is deformed in dependence on the size of a pressure acting on the sensor head 30. Through the reflection on the membrane the light exiting from the optical fiber 28A is reflected modulatingly and coupled back into the optical fiber. At the proximal end of the optical fiber 28A, i.e. in the evaluation device 100, there is located a digital camera, e.g. a CCD camera or a CMOS, which evaluates the incoming light in the form of an interference pattern. In dependence thereon, a pressure-dependent electrical signal is generated. The evaluation of the optical image or optical pattern delivered by the camera and the computation of the pressure are effected by a computer attached to the camera, which also controls the power supply to the motor-operated pumping device 50 in dependence on the effected evaluation of the pressure signal.

According to the invention, at least the optical fiber 28A also serves as a kink sensor and thus performs a second functionality. It is also possible, however, to provide a separate optical fiber in the catheter hose 20 and, where applicable, beyond the catheter hose as a kink sensor. In this case, the sensor head 30 does not have to be so complicated in structure, as explained with reference to FIG. 2, but it suffices when the distal end area 33 of the optical fiber 28A reflects the light transmitted in the optical fiber 28A. The same evaluation device 100 can be employed and only has to be arranged for measuring the extent to which the light quantity coupled into the optical fiber 28A comes back. For this purpose, the quantity of light captured per time unit by the CCD camera or another light-sensitive device can be added up and any fluctuations captured and displayed as a kink event. Depending on the quantity of light coupled out, a bend radius can also be inferred before an actual kink event occurs.

The invention claimed is:

1. An intravascular blood pump comprising:
 a pumping device; and
 a system comprising a catheter having a kink sensor, wherein the kink sensor comprises at least one optical fiber having a first end and a second end, the optical fiber is part of an optical pressure sensor, the kink sensor possesses a sensor head firmly connected to the pumping device;
 the system further comprising an evaluation device attached to the optical fiber of the catheter, wherein the evaluation device is arranged for evaluating a preset light quantity transmitted through the optical fiber as to whether a part of the light quantity is coupled out of the optical fiber along the length of the optical fiber.

2. The blood pump according to claim 1, wherein the kink sensor extends over the total length of the catheter and is arranged for detecting a kinking of the catheter over the total length of the catheter.

3. The blood pump according to claim 1, wherein the optical fiber has segments with different light-transmitting properties.

4. The blood pump according to claim 1, wherein the kink sensor has a plurality of optical fibers of different length.

5. The blood pump according to claim 1, wherein the optical fiber comprises a glass fiber and possesses a diameter of 120 µm or less.

6. The blood pump according to claim 1, wherein the optical fiber comprises a plastic fiber and possesses a diameter of 250 µm or less.

7. The blood pump according to claim 1, wherein the optical fiber is laid freely movably in a lumen which consists of a material comprising a shape-memory alloy.

8. The blood pump according to claim 1, wherein the optical fiber is laid freely movably in a lumen which consists of a polymer material which is anti-friction-coated on the inside.

9. The blood pump according to claim 1, wherein the pressure sensor has a sensor head which is disposed on a distal, soft-flexible tip of the catheter.

10. The blood pump according to claim 1, wherein the evaluation device is arranged for generating an alarm when the coupled-out part of the light quantity reaches or exceeds a preset limiting value.

11. The system according to claim 1, wherein the optical pressure sensor comprises a membrane configured to be deformed in dependence on the pressure acting on the sensor head, to reflect light exiting the optical fiber and to feed the reflected light back into the optical fiber.

12. The blood pump of claim 1, wherein:
the kink sensor extends along the pumping device.

13. The blood pump of claim 1, wherein:
the pumping device comprises a flexible flow cannula with a suction inlet; and
the kink sensor extends along said cannula.

* * * * *